United States Patent
Kang et al.

(10) Patent No.: US 10,660,684 B2
(45) Date of Patent: May 26, 2020

(54) SURGICAL SCREW AND FUSION DEVICE USING SAME

(71) Applicant: L & K BIOMED CO., LTD., Yongin-si, Gyeonggi-do (KR)

(72) Inventors: Gook-Jin Kang, Seoul (KR); Sun Kak Choi, Gwangju-si (KR)

(73) Assignee: L&K BIOMED CO., LTD., Yongin-si, Gyeonggi-do (KR)

( * ) Notice: Subject to any disclaimer, the term of this patent is extended or adjusted under 35 U.S.C. 154(b) by 105 days.

(21) Appl. No.: 15/768,791

(22) PCT Filed: Jun. 23, 2016

(86) PCT No.: PCT/KR2016/006654
§ 371 (c)(1),
(2) Date: Apr. 16, 2018

(87) PCT Pub. No.: WO2017/069374
PCT Pub. Date: Apr. 27, 2017

(65) Prior Publication Data
US 2018/0303530 A1 Oct. 25, 2018

(30) Foreign Application Priority Data
Oct. 19, 2015 (KR) .................. 10-2015-0145414

(51) Int. Cl.
*A61B 17/04* (2006.01)
*A61B 17/86* (2006.01)
(Continued)

(52) U.S. Cl.
CPC .......... *A61B 17/8685* (2013.01); *A61B 17/70* (2013.01); *A61B 17/72* (2013.01);
(Continued)

(58) Field of Classification Search
CPC combination set(s) only.
See application file for complete search history.

(56) References Cited

U.S. PATENT DOCUMENTS 6,398,783 B1 6/2002 Michelson
7,625,379 B2 12/2009 Puno et al.
(Continued)

FOREIGN PATENT DOCUMENTS

| KR | 10-2007-0084011 A | 8/2007 |
|---|---|---|
| KR | 10-1040515 B1 | 6/2011 |
| KR | 10-2011-0106863 A | 9/2011 |

OTHER PUBLICATIONS

English translation of International Search Report for PCT/KR2016/006654, dated Sep. 22, 2016.
(Continued)

*Primary Examiner* — Sameh R Boles
(74) *Attorney, Agent, or Firm* — Medler Ferro Woodhouse Mills PLLC (57) ABSTRACT

The present invention relates to a surgical screw capable of self-locking and a fusion device using the same. The surgical screw includes: a screw body having a body thread formed on an outer circumferential surface thereof, and a body driving groove formed in an upper portion thereof; and a head part rotatably fixed with respect to the screw body so as to be moved in an axial direction of the screw body, wherein, when the head part rotates relative to the screw body, the head part is spaced apart from the screw body with a predetermined distance, thereby causing the threads of the head part and the screw body to become discontinuous, and thus the surgical screw is brought into a locked state. The surgical screw may also be included in a fusion device in a different form by coupling with a plate or a cage.

5 Claims, 12 Drawing Sheets

(51) Int. Cl.
- *A61F 2/08* (2006.01)
- *A61B 17/70* (2006.01)
- *A61B 17/72* (2006.01)
- *A61F 2/44* (2006.01)

(52) U.S. Cl.
CPC .......... *A61B 17/86* (2013.01); *A61B 17/8605* (2013.01); *A61B 17/8625* (2013.01); *A61F 2/44* (2013.01)

(56) References Cited

U.S. PATENT DOCUMENTS

| | | |
|---|---|---|
| 7,846,207 B2 | 12/2010 | Lechmann et al. |
| 8,075,604 B2 | 12/2011 | Denis et al. |
| 8,328,872 B2 | 12/2012 | Duffield et al. |
| 8,449,585 B2 | 5/2013 | Wallenstein et al. |
| 8,795,373 B2 | 8/2014 | Jones et al. |
| 2013/0226245 A1* | 8/2013 | Wallenstein ....... A61B 17/8605 606/279 |

OTHER PUBLICATIONS

English translation of International Search Report for PCT/KR2016/006656, dated Sep. 22, 2016.

* cited by examiner

SURGICAL SCREW AND FUSION DEVICE USING SAME

TECHNICAL FIELD

The present invention relates to a surgical screw and a fusion device using the same, and more particularly, to a surgical screw capable of self-locking and a fusion device using the same.

BACKGROUND ART

Various types of fasteners are used to fasten implants and other devices to bones. In a spinal field, bone screws are typically used in order to attach plates, rods, and the like of implants and devices to one or more vertebral bodies.

Various techniques have been developed to fix the bone screws to the vertebral bodies, or prevent the bone screws from being separated from the plates or rods of the implants and devices. For example, U.S. Pat. No. 7,846,207 discloses a technique in which a cage may be inserted between vertebral bodies and bone screws may be attached to the vertebral bodies to fix the cage. The above patent proposes a method in which, a securing plate is further provided on a head side of the bone screw to prevent the bone screw from being pulled out, and the securing screw is coupled to the cage by passing it through the securing plate.

In addition, U.S. Pat. No. 6,398,783 discloses a locking element that rotates around a hole into which the bone screw is inserted, which is installed in a plate to prevent the bone screw from being pulled out when fixing the plate to the vertebral body.

Further, U.S. Pat. No. 7,625,379 discloses using two nuts in an SI joint fusion implant to prevent the bone screw from being pulled out, which is used when a problem occurs in a joint between a sacrum and an ilium (pelvis).

As such, various techniques for preventing the bone screw from being pulled out in various areas are considered and disclosed in the art, but there is a disadvantage that a separate locking mechanism should be used for this purpose. Therefore, there is a need to develop a screw which can easily maintain the locked state without the separate locking mechanism.

PRIOR ART DOCUMENT

Patent Document (Patent Document 1) U.S. Pat. No. 7,846,207
(Patent Document 2) U.S. Pat. No. 6,398,783
(Patent Document 3) U.S. Pat. No. 7,625,379

SUMMARY OF INVENTION

Problems to be Solved by Invention

In consideration of the above-mentioned circumstances, it is an object of the present invention to provide a surgical screw capable of self-locking without a separate locking mechanism and a fusion device using the same.

Means for Solving Problems

In order to achieve the above object, according to an aspect of the present invention, there is provided a surgical screw including: a screw body having a body thread formed on an outer circumferential surface thereof, and a body driving groove formed in an upper portion thereof; and a head part which is rotatably fixed with respect to the screw body so as to be moved in an axial direction of the screw body, and has a head thread formed on an outer circumferential surface thereof to be continued to the body thread and an inner space communicating with the body driving groove, wherein the screw body and the head part have a body sliding part and a head sliding part, which are formed at an end portion thereof, respectively, and are configured to abut each other, and the body sliding part and the head sliding part have a recess formed in one part thereof and a protrusion formed on the other part thereof to be inserted into the recess, such that when the head part relatively rotates with respect to the screw body, the protrusion is separated from the recess and comes in contact with any one of the body sliding part and the head sliding part, thereby allowing the head part to be spaced apart from the screw body in an axial direction thereof.

The head part may be configured to move within a limited distance in the axial direction of the screw body.

The body thread may include a body main thread and a body auxiliary thread, and the body auxiliary thread is continued to the head thread.

The head part may have a head driving hole formed therein, and the head driving hole may have the same cross-sectional shape and cross-sectional area as those of the body driving groove of the screw body.

The surgical screw further includes a sleeve which is configured to surround the head part and an upper portion of the screw body, and has a sleeve thread screwed with both the body thread and the head thread, wherein the sleeve thread is screwed with both the body thread and the head thread even in a state in which the head part is spaced apart from the screw body in the axial direction of the screw body.

In addition, according to another aspect of the present invention, there is provided a fusion device including: the surgical screw according to the present invention; and a plate in which the surgical screw is installed.

Further, according to another aspect of the present invention, there is provided a fusion device including: the surgical screw according to the present invention; and a cage having a through hole in which the surgical screw penetrates.

Advantageous Effects

According to the present invention, it is possible to provide a surgical screw which can easily maintain a locked state without a separate locking mechanism and a fusion device including the same. In addition, since the surgical screw has no separate locking mechanism, there is an advantage that the number of tools for locking the screw is reduced, and the operator's labor and procedure time are reduced.

MODE FOR CARRYING OUT INVENTION

The present invention has an object to provide a surgical screw capable of self-locking without a separate locking mechanism and a fusion device using the same.

Hereinafter, the present invention will be described in detail with reference to the accompanying drawings. In denoting reference numerals to constitutional elements of respective drawings, it should be noted that the same elements will be denoted by the same reference numerals although they are illustrated in different drawings. In the embodiments of the present invention, the publicly known functions and configurations that are judged to be able to make the purport of the present invention unnecessarily obscure will not be described.

FIGS. 1 to 6 illustrate a surgical screw 100 according to Embodiment 1 of the present invention. The surgical screw 100 includes: a screw body 102 having a body thread formed on an outer circumferential surface thereof, and a body driving groove 110 formed in an upper portion thereof; and a head part 104 which is rotatably fixed with respect to the screw body 102 so as to be moved in an axial direction of the screw body 102, and has a head thread 118 formed on an outer circumferential surface thereof to be continued to the body thread and an inner space communicating with the body driving groove 110.

The body thread may include a body main thread 116 and a body auxiliary thread 119. In this case, the body main thread 116 and the body auxiliary thread 119 may be formed spaced apart from each other, or may have different pitches or diameters from each other.

The screw body 102 has a body sliding part 114 formed at an upper end portion thereof, and the head part 104 has a head sliding part 122 formed at a lower end portion thereof. The body sliding part 114 and the head sliding part 122 are configured to rotate with being in contact with each other (see FIG. 4). In order to allow the head part 104 to rotate with respect to the screw body 102, the screw body 102 has a connecting part 106 formed at the upper portion thereof with protruding upward from the body sliding part. The head part 104 may be coupled to the connecting part 106 so as to be mounted thereon.

The connecting part 106 has a connecting part engaging jaw 108 formed at an upper outer circumference thereof, and the head part 104 has a head part engaging jaw formed at a lower inner circumference thereof. By abutment of these engaging jaws, the head part 104 can move within a limited distance in the axial direction of the screw body 102 (see FIG. 5).

Further, the body sliding part 114 has a recess 112 formed in an upper end thereof, and the head sliding part 122 has a protrusion 124 formed on a lower end thereof. On the other hand, the protrusion may be formed on the upper end of the body sliding part 114 and the recess may be formed in the lower end of the head sliding part 122. The protrusion 124 is inserted into the recess 112, and when applying an external force thereto, the protrusion 124 can be brought into contact with the body sliding part 114 out of the recess 112. As a result, when the head part 104 relatively rotates with respect to the screw body 102, the head part 104 may be spaced apart from the screw body 102 in the axial direction thereof (see FIG. 6).

As a result, threads of the head thread 118 and the body thread may become unaligned with respect to each other. Therefore, a direction of a force applied by the body thread of the screw body 102 to the periphery thereof and a direction of a force applied by the head thread 118 of the head part 104 to the periphery thereof may be opposite to each other, and thereby bring the surgical screw 100 into a locked state.

Figure 1:
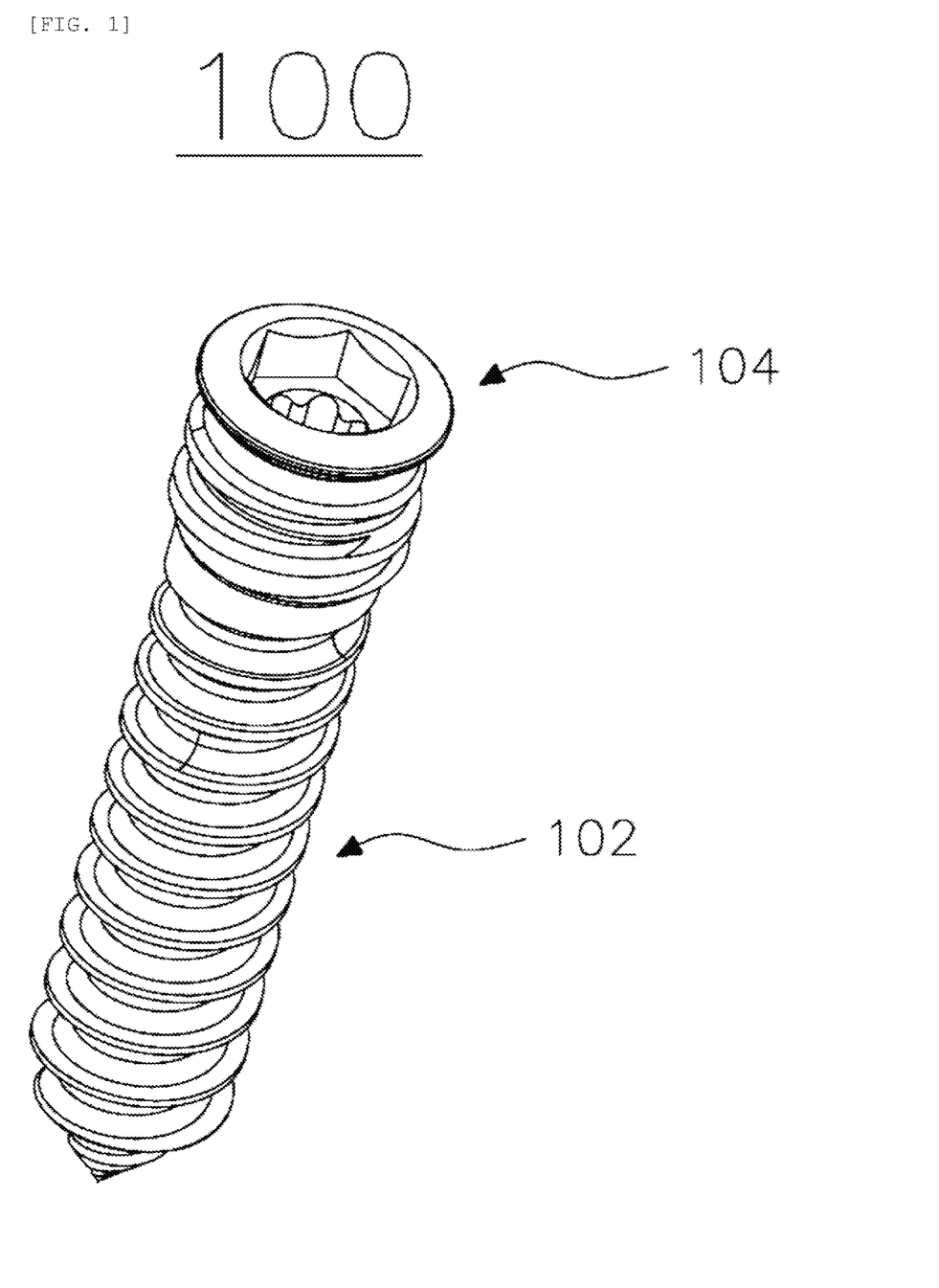
FIG. 1 is a perspective view illustrating a surgical screw according to Embodiment 1 of the present invention.
Figure 2:
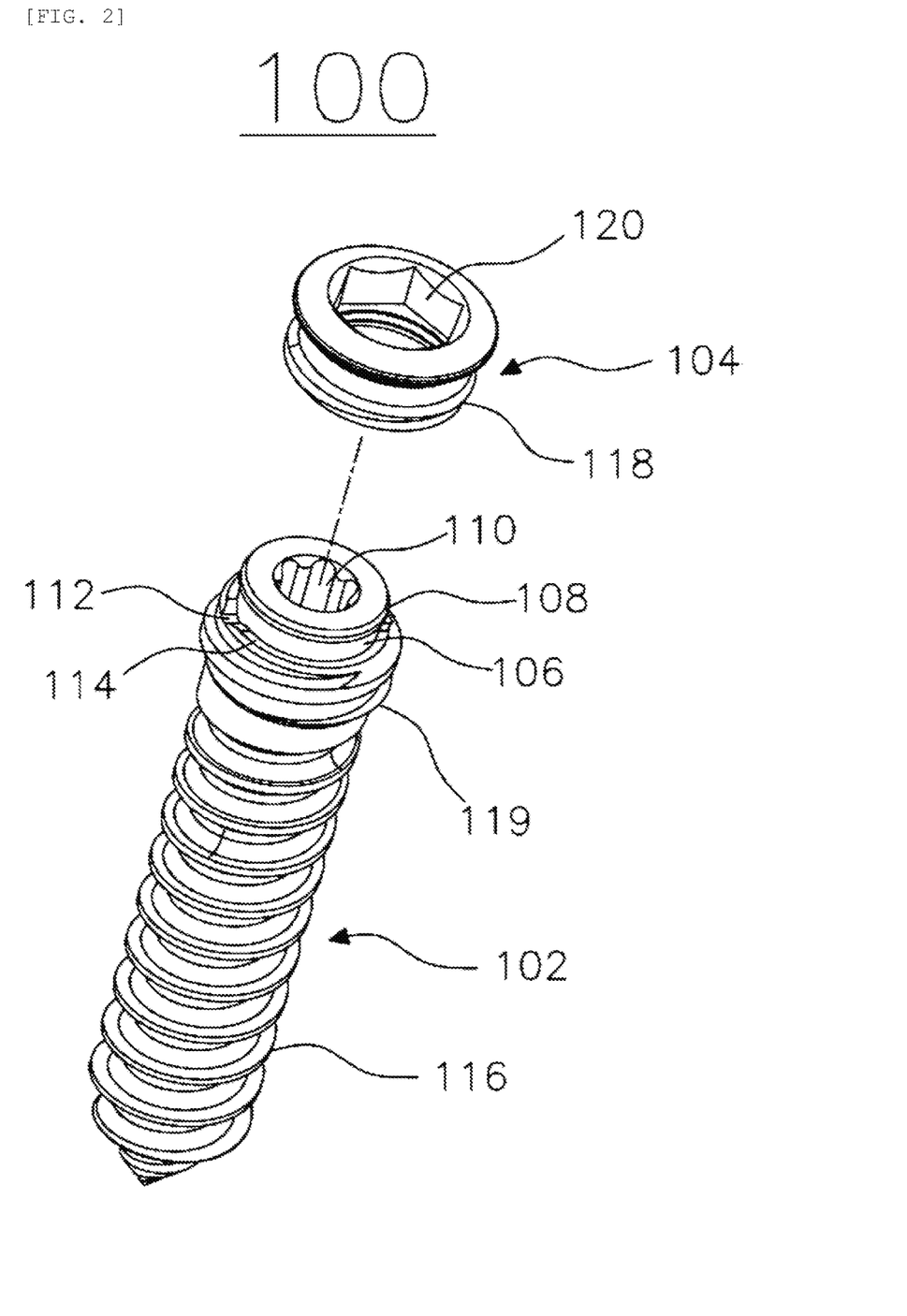
FIG. 2 is an exploded perspective view of the surgical screw of FIG. 1 viewed from a top side.
Figure 3:
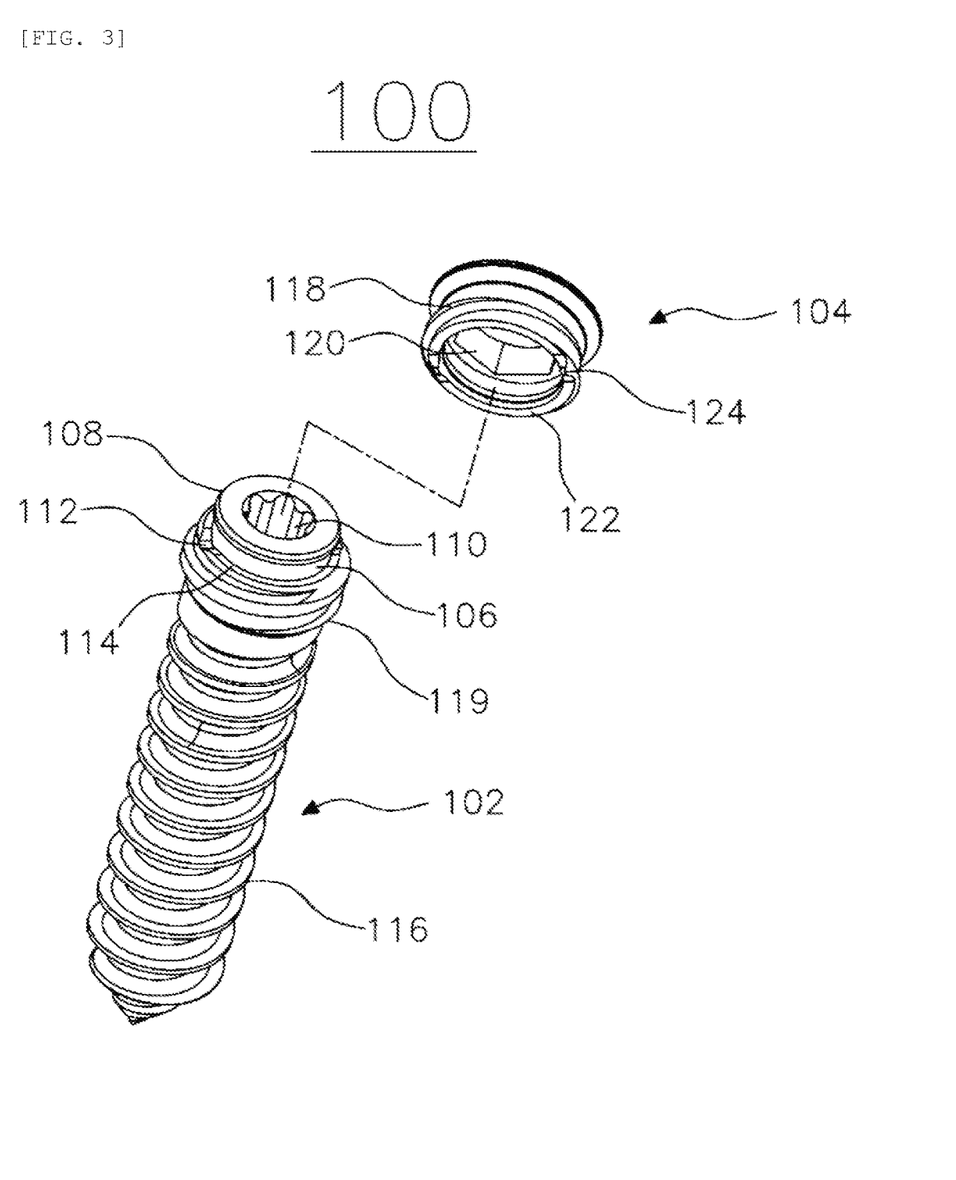
FIG. 3 is an exploded perspective view of the surgical screw of FIG. 1 when viewing a head part from a bottom side.
Figure 4:
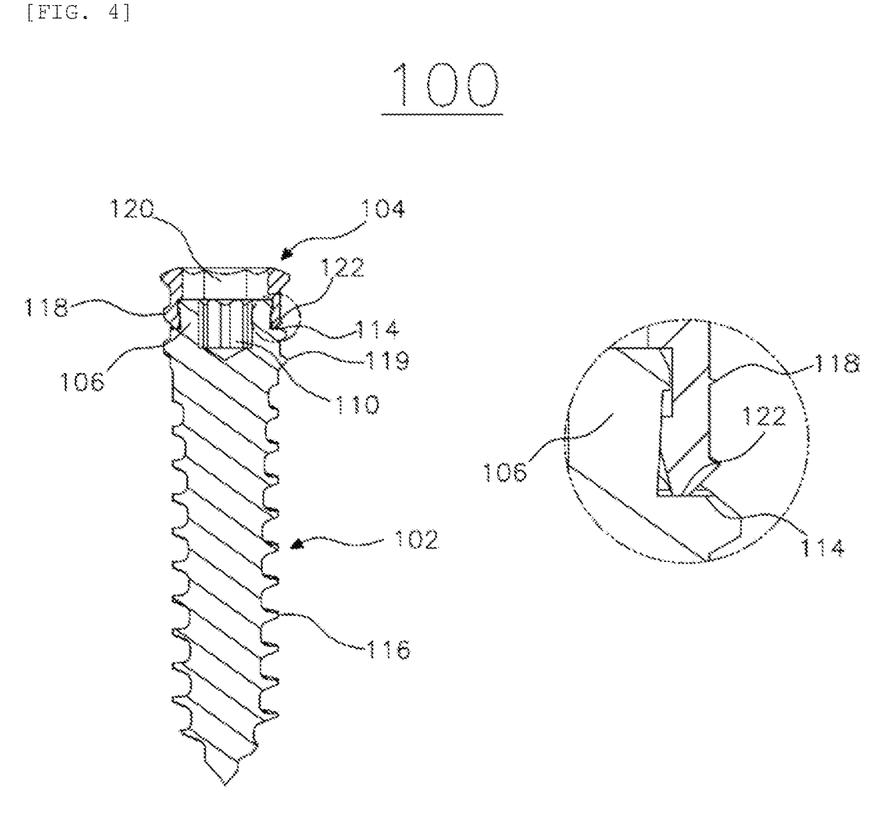
FIG. 4 is a cross-sectional view illustrating a state in which the surgical screw of FIG. 1 is pulled out.
Figure 5:
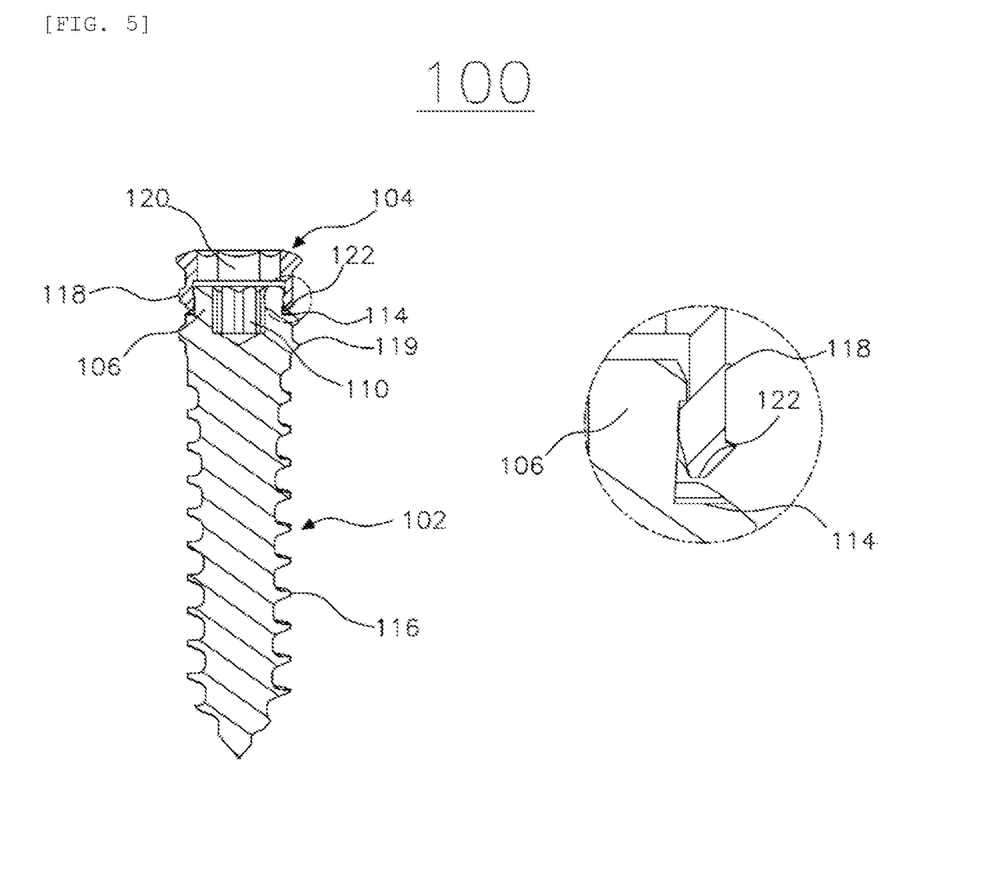
FIG. 5 is a cross-sectional view illustrating a state in which the surgical screw of FIG. 1 is locked.
Figure 6:
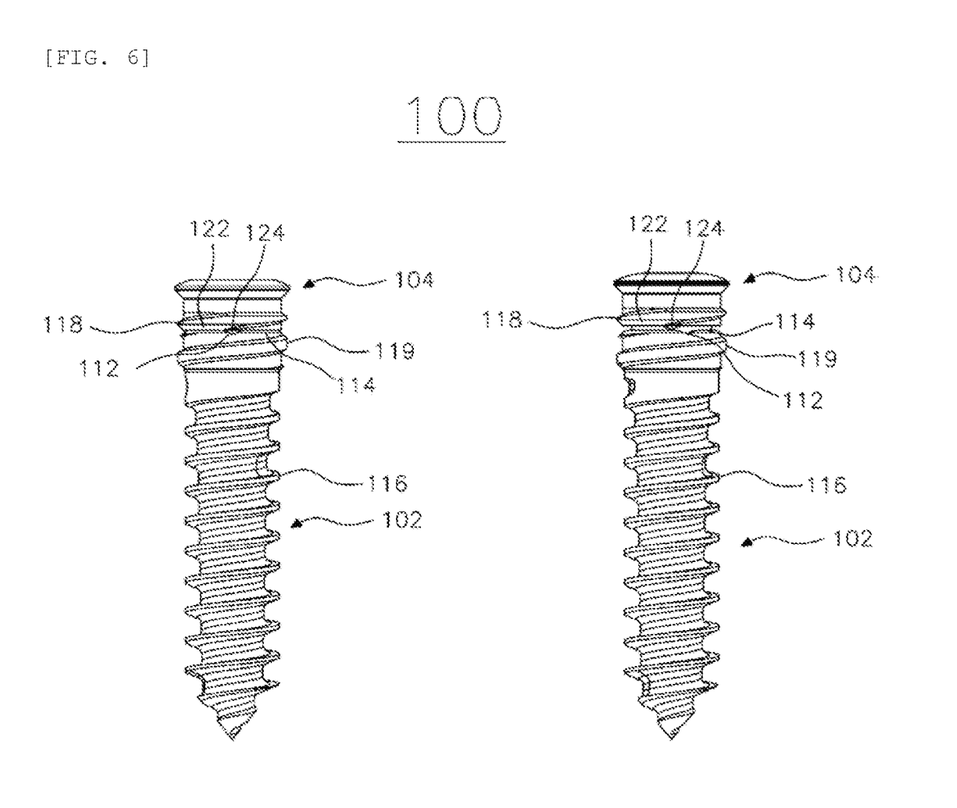
FIG. 6 is front views illustrating states in which the surgical screws of FIG. 1 are pulled out and locked.
Figure 7:
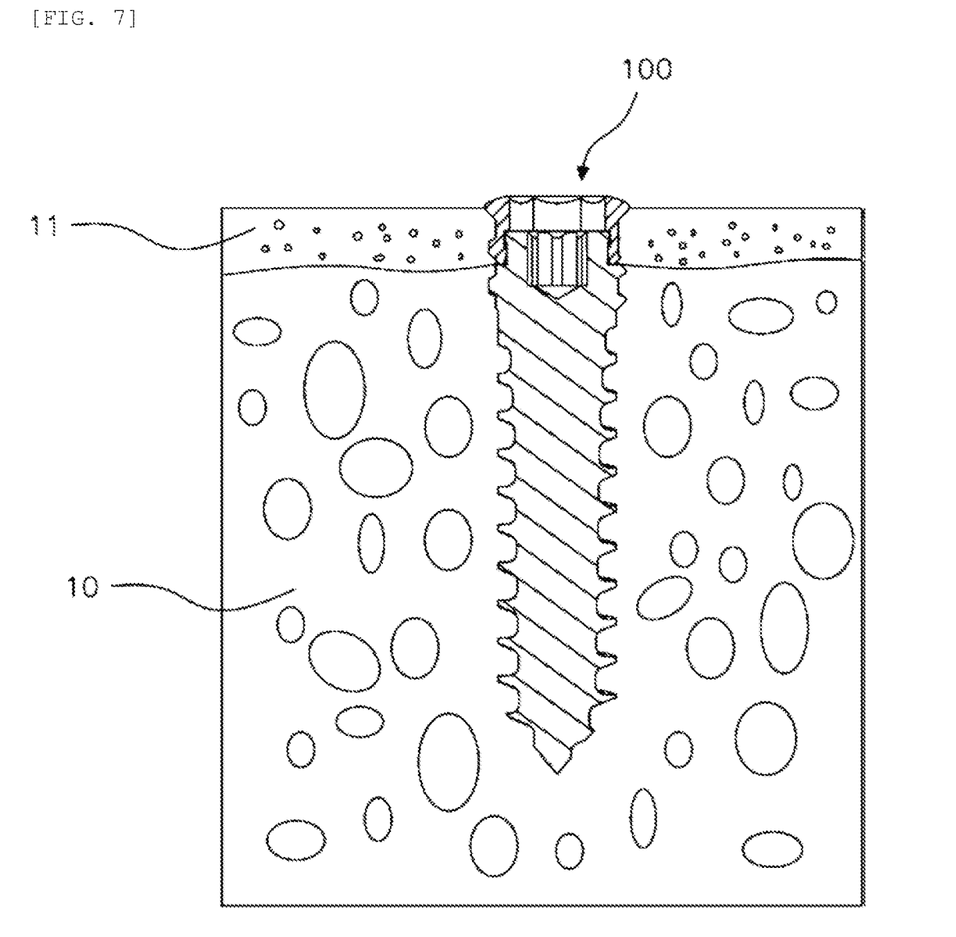
FIG. 7 is a sectional view illustrating a state in which the surgical screw of FIG. 1 is installed in a bone.

As illustrated in FIG. 7, when inserting the surgical screw 100 into a bone, the head part 104 is first inserted into a female screw which is formed in the bone by inserting the screw body 102 while rotating together therewith. At this time, when further rotating any one of the head part 104 and the screw body 102, the head part 104 and the screw body 102 are pressed to the above-described female screw in the directions opposite to each other while being spaced apart from each other, and thereby they bring into a locked state based on the same principle as a lock nut. In particular, when inserting the surgical screw 100 into bone tissues different from each other such as a cortical bone 11 and a cancellous bone 10, the head part 104 is brought into the locked state in the cortical bone 11, while forming a large frictional force. Thereby, it is possible to achieve the same performance as the existing SI joint with only one screw.

Of course, in order to release the locked state, when the protrusion 124 is inserted into the recess 112 by forcibly rotating only any one of the head part 104 and the screw body 102, the head part 104 and the screw body 102 are close to each other, such that the threads of the body thread and the head thread 118 become aligned with each other. Therefore, the surgical screw 100 may be brought into a pulled out state, and thereby be removed with a screwdriver or the like.

Figure 8:
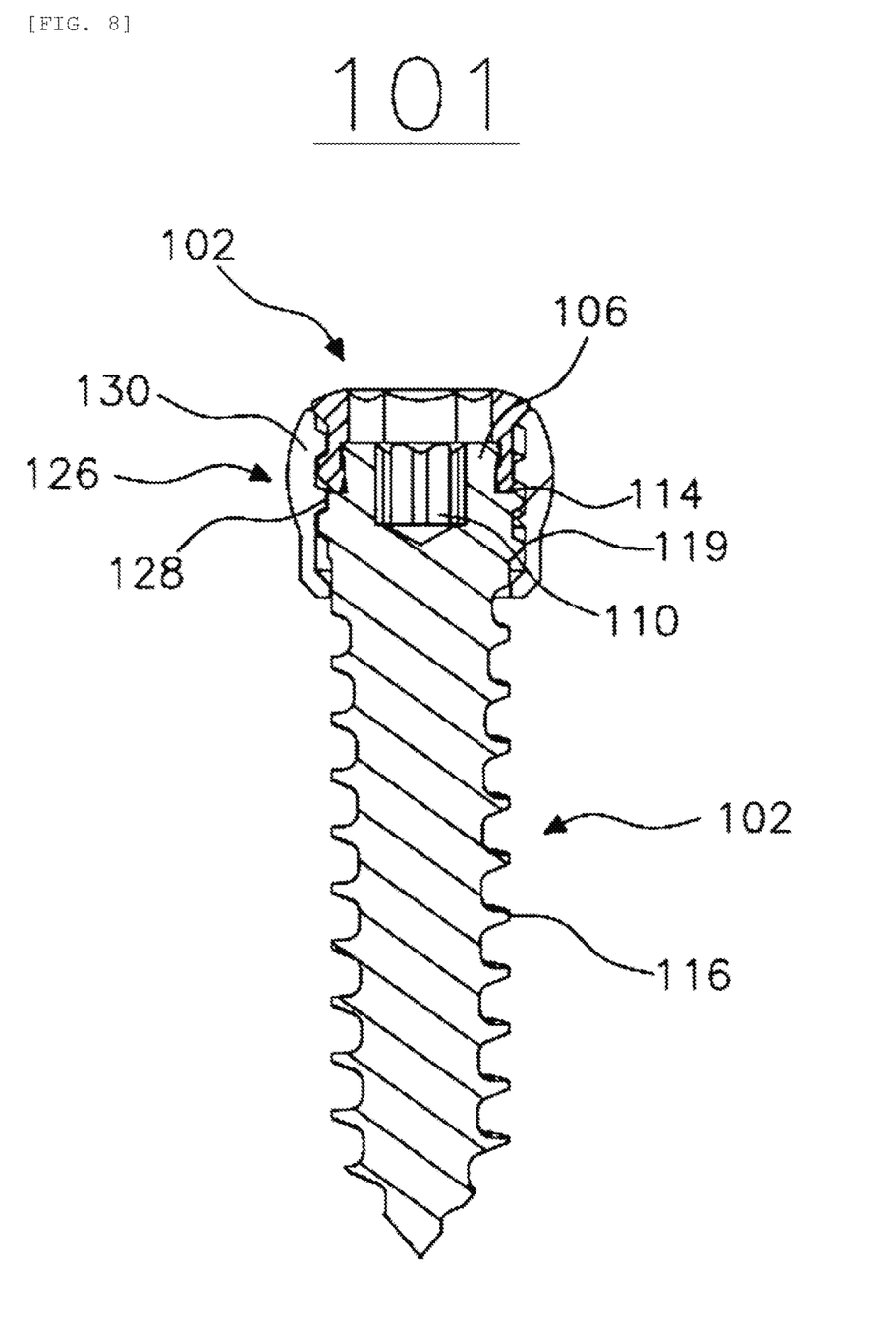
FIG. 8 is a cross-sectional view illustrating a surgical screw according to Embodiment 2 of the present invention.

FIG. 8 illustrates a surgical screw 101 according to Embodiment 2 of the present invention. The surgical screw 101 further includes a sleeve 126 configured to surround the head part 104 and the upper portion of the screw body 102. The sleeve 126 has a sleeve thread 128 which is screwed with both the body auxiliary thread 119 and the head thread 118. The sleeve 126 has a sleeve body 130 which may be formed in various shapes as necessary and may be rotated in a plate, a cage, or the like when an outer circumference thereof is formed in a spherical surface.

The sleeve thread 128 should have a lead height sufficient to be screwed with both the body auxiliary thread 119 and the head thread 118 even in a state in which the head part 104 is spaced apart from the screw body 102 in the axial direction of the screw body 102.

Figure 9:
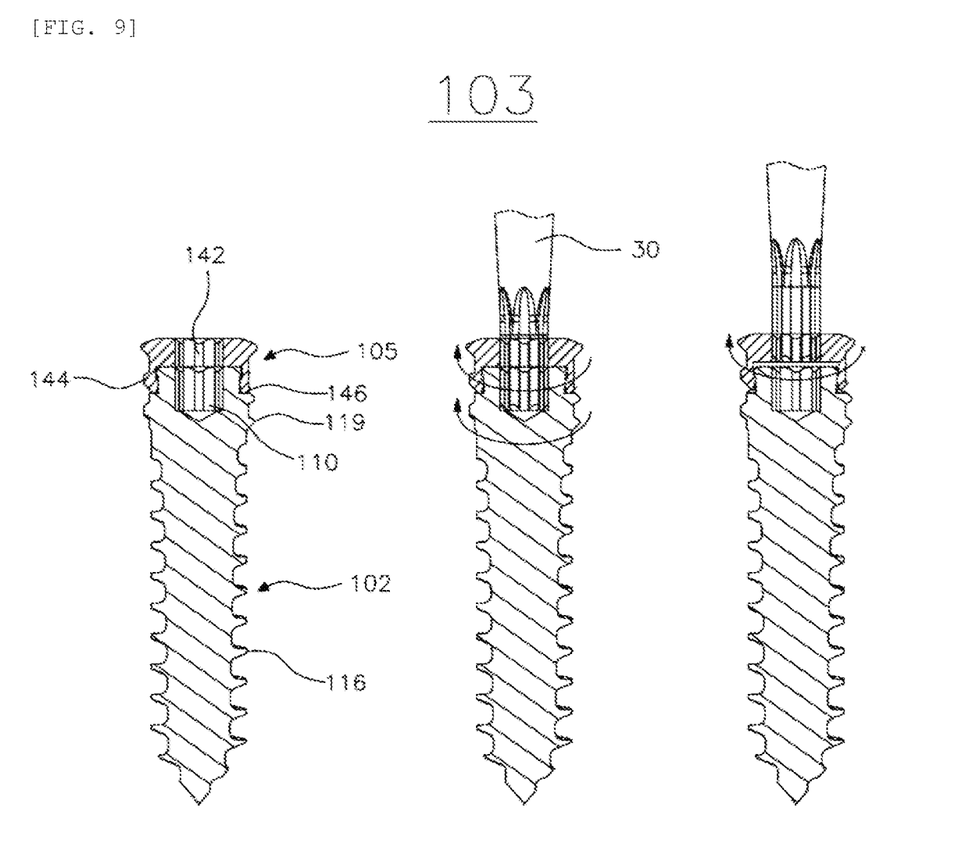
FIG. 9 is perspective views illustrating a surgical screw according to Embodiment 3 of the present invention.

FIG. 9 illustrates a surgical screw 103 according to Embodiment 3 of the present invention. The surgical screw 103 is characterized by having a head driving hole 142 formed in the head part 105, and other components such as a head thread 144 and a head sliding part 146 are the same as those of the head part 104 of Embodiment 1. That is, the head driving hole 142 has the same cross-sectional shape and cross-sectional area as those of the body driving groove 110 of the screw body 102. As a result, as illustrated in FIG. 9, all operations of insertion, switching of the locked state, switching of the unlocked state, and discharge of the surgical screw 103 may be performed only by changing an insertion level of one screwdriver between the head driving hole and the body driving groove.

Figure 10:
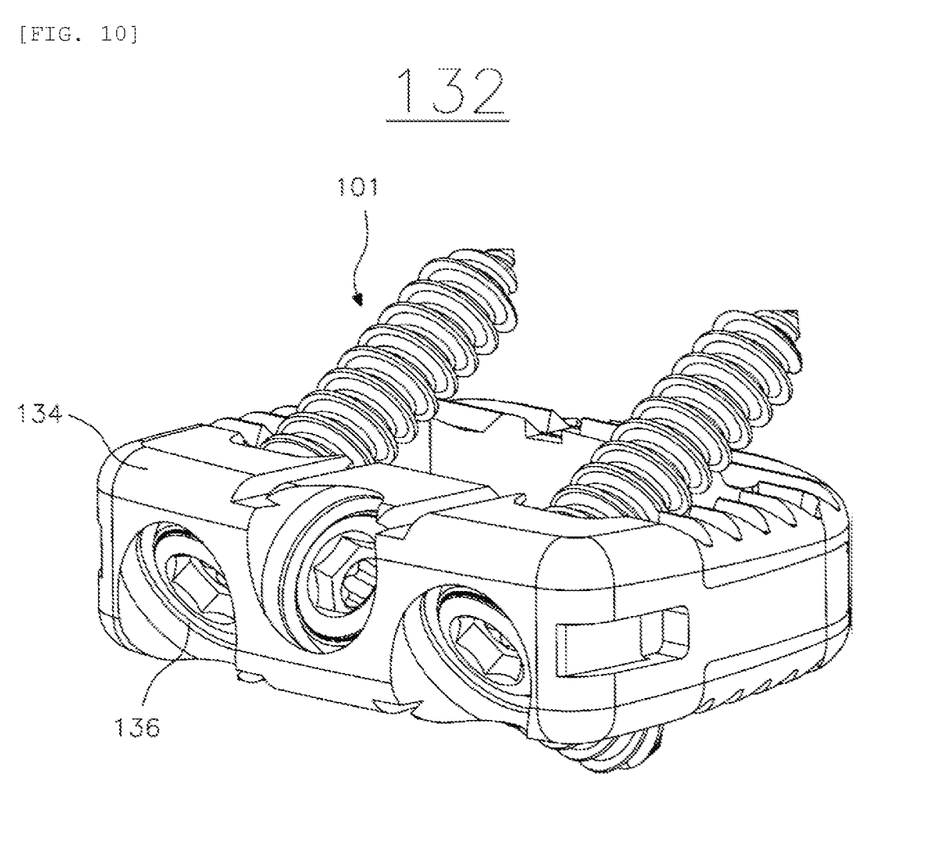
FIG. 10 is a perspective view illustrating an example of a fusion device using the surgical screw according to Embodiment 2.
Figure 11:
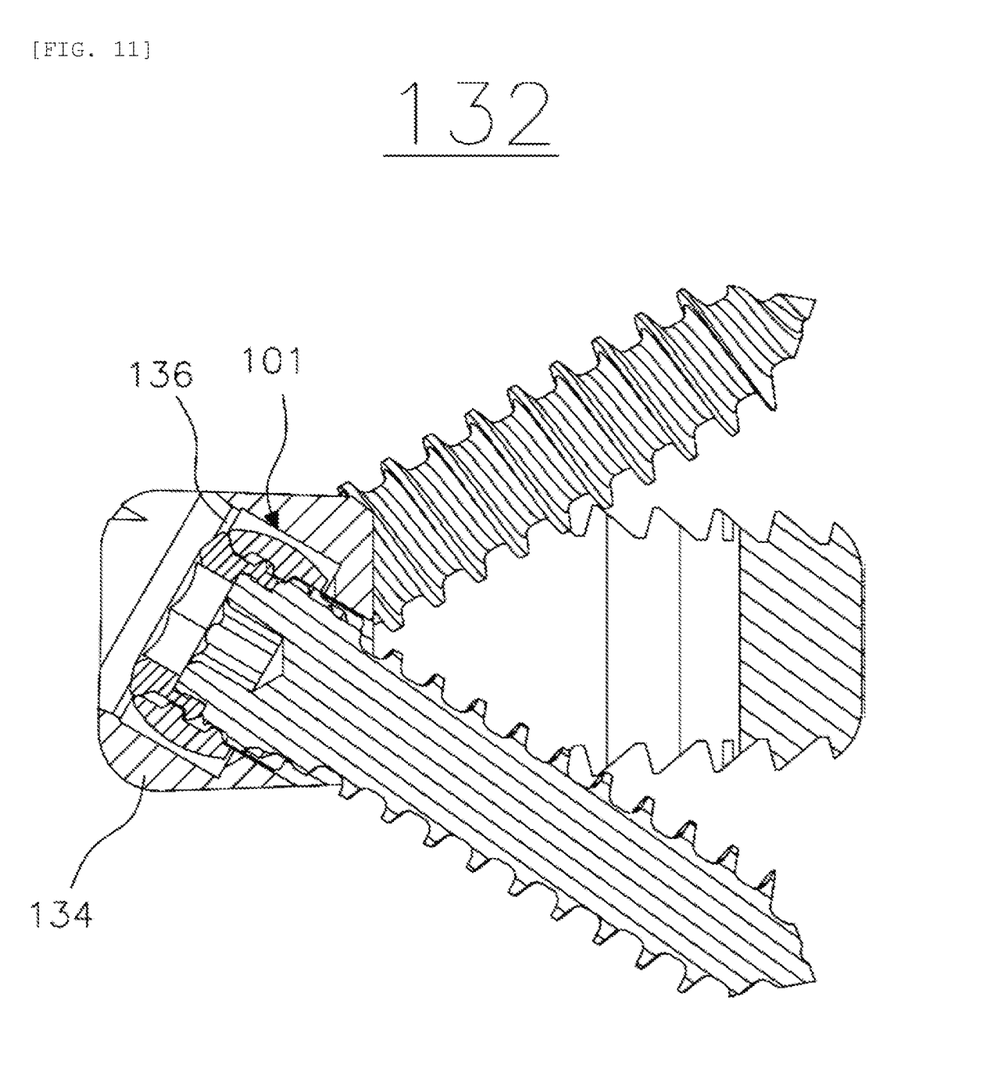
FIG. 11 is a cross-sectional view of the fusion device of FIG. 10.

FIGS. 10 and 11 illustrate a fusion device 132 using the surgical screw 101 according to Embodiment 2 of the present invention. The fusion device 132 includes a cage 134 inserted between vertebral bodies, and the surgical screws 101 inserted into through holes 136 formed in the cage 134. Since the surgical screw 101 has the sleeve 126, the surgical screw 101 can rotate within the through hole 136 in a predetermined range. Since the surgical screws 100 are screwed with the vertebral bodies while the surgical screws 100 are self-locked to the cage 134, there is an advantage that an additional locking device is not required. Of course, it is also possible to use the surgical screws 100 and 105 of Embodiments 1 and 3 in the fusion device. In this case, the surgical screw 100 is fixed in a predetermined direction without being rotated inside the through hole.

Figure 12:
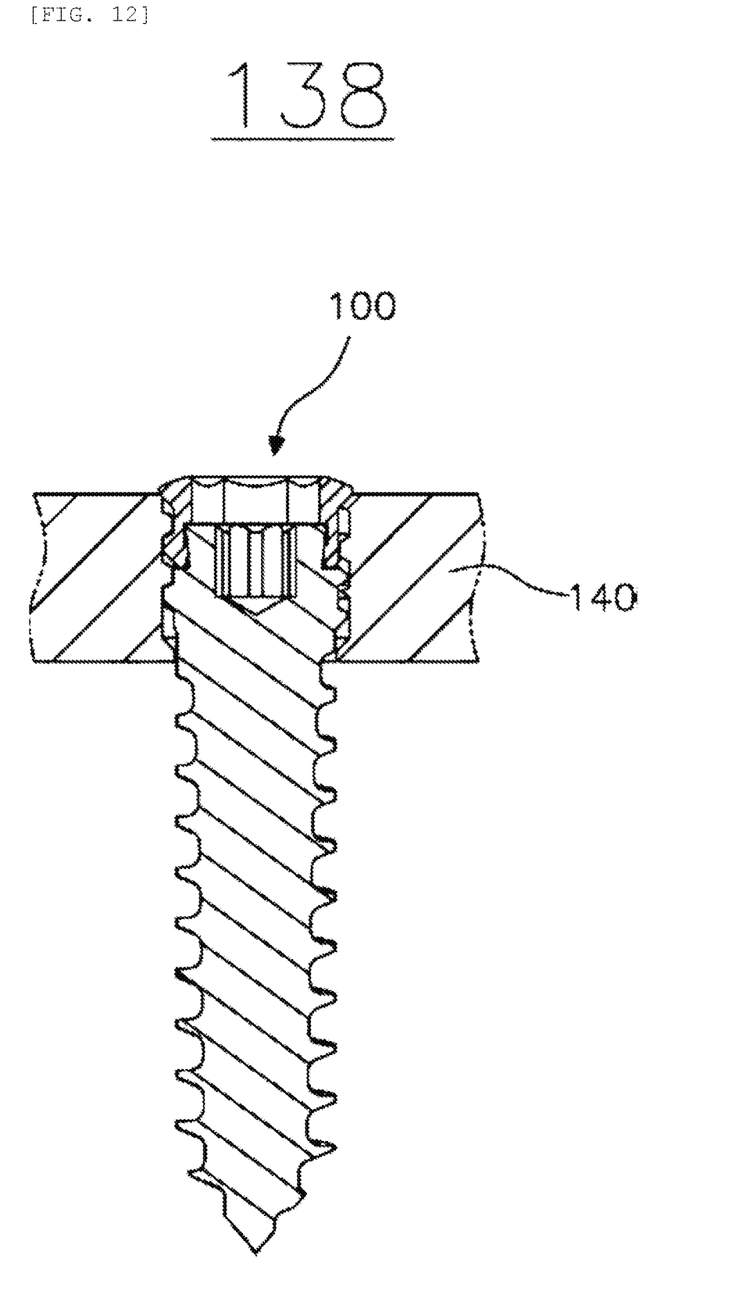
FIG. 12 is a cross-sectional view illustrating another example of the fusion device using the surgical screw according to Embodiment 1.

FIG. 12 illustrates a fusion device 138 using the surgical screw 100 according to Embodiment 1 of the present invention. The fusion device 138 includes a plate 140 which is in contact with the bone such as a vertebral body, and the surgical screw 100 which is installed in the plate 140. Therefore, since the surgical screw 100 is fixed to the plate 140 and self-locked, there is an advantage that an additional locking device is not required. Of course, it is also possible to use the surgical screws 103 and 105 according to Embodiments 2 and 3 in the fusion device.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims.

DESCRIPTION OF REFERENCE NUMERALS

10: Cancellous bone
11: Cortical bone
100, 101: Surgical screw
102: Screw body
104, 105: Head part
106: Connecting part
108: Connecting part engaging jaw
110: Body driving groove
112: Recess
114: Body sliding part
116: Body main thread
118, 144: Head thread
119: Body auxiliary thread
120, 142: Head driving hole
122, 146: Head sliding part
124: Protrusion
126: Sleeve
128: Sleeve thread
130: Sleeve body
132, 138: Fusion device
134: Cage
136: Through hole
140: Plate

INDUSTRIAL APPLICABILITY

According to the present invention, it is possible to provide a surgical screw which can easily maintain a locked state without a separate locking mechanism and a fusion device including the same. In addition, since the surgical screw has no separate locking mechanism, there is an advantage that the number of tools for locking the screw is reduced, and the operator's labor and procedure time are reduced.

The invention claimed is:

1. A surgical screw comprising:
a screw body having a body thread formed on an outer circumferential surface thereof, and a body driving groove formed in an upper portion thereof; and
a head part which is rotatably fixed with respect to the screw body so as to be moved in an axial direction of the screw body, and has a head thread formed on an outer circumferential surface thereof to be continued to the body thread and an inner space communicating with the body driving groove,
wherein the screw body and the head part have a body sliding part and a head sliding part, which are formed at an end portion thereof, respectively, and are configured to abut each other, and
the body sliding part and the head sliding part have a recess formed in one part thereof and a protrusion formed on the other part thereof to be inserted into the recess, such that when the head part relatively rotates with respect to the screw body, the protrusion is separated from the recess and comes in contact with any one of the body sliding part and the head sliding part, thereby allowing the head part to be spaced apart from the screw body in an axial direction thereof.

2. The surgical screw according to claim 1, wherein the head part is configured to move within a limited distance in the axial direction of the screw body.

3. The surgical screw according to claim 1, wherein the body thread includes a body main thread and a body auxiliary thread, and the body auxiliary thread is continued to the head thread.

4. The surgical screw according to claim 1, wherein the head part has a head driving hole formed therein, and the head driving hole has the same cross-sectional shape and cross-sectional area as those of the body driving groove of the screw body.

5. The surgical screw according to claim 1, further comprising a sleeve which is configured to surround the head part and an upper portion of the screw body, and has a sleeve thread screwed with both the body thread and the head thread, wherein the sleeve is screwed with both the body thread and the head thread even in a state in which the head part is spaced apart from the screw body in the axial direction of the screw body.

* * * * *